United States Patent [19]

Banholzer et al.

[11] Patent Number: 4,608,377

[45] Date of Patent: Aug. 26, 1986

[54] QUATERNARY 6,11-DIHYDRO-DIBENZO-[B,E]-THIEPINE-11-N-ALKYLNORSCOPINE ETHERS HAVING SPASMOLYTIC ACTIVITY

[75] Inventors: Rolf Banholzer, Ingelheim; Rudolf Bauer, Wiesbaden, both of Fed. Rep. of Germany

[73] Assignee: Boehringer Ingelheim KG, Ingelheim am Rhein, Fed. Rep. of Germany

[21] Appl. No.: 623,963

[22] Filed: Jun. 25, 1984

Related U.S. Application Data

[63] Continuation of Ser. No. 471,353, Mar. 2, 1983, abandoned.

[30] Foreign Application Priority Data

Mar. 26, 1982 [DE] Fed. Rep. of Germany ....... 3211185

[51] Int. Cl.$^4$ .................. C07D 491/08; A61K 31/46
[52] U.S. Cl. ....................................... 514/291; 546/91

[58] Field of Search ......................... 546/91, 126, 124; 514/291

[56] References Cited

U.S. PATENT DOCUMENTS 3,413,296 11/1968 Jucker et al. ....................... 546/124

OTHER PUBLICATIONS

Chemical Abstracts, vol. 82, No. 16, Abst. No. 103,152y, pub. Apr. 21, 1975.

Burger's Medicinal Chemistry, Fourth Edition, Part III, pp. 370–377 and 420, edited by Manfred E. Wolff, 1979.

*Primary Examiner*—Alan L. Rotman
*Attorney, Agent, or Firm*—Hammond & Littell, Weissenberger & Dippert

[57] ABSTRACT

The invention herein relates to novel quaternary 6,11-dihydro-dibenzo-[b,e]-thiepine-11-N-alkylnorscopine ethers, the preparation thereof, and their use as spasmolytics or bronchospasmolytics.

18 Claims, No Drawings

QUATERNARY 6,11-DIHYDRO-DIBENZO-[B,E]-THIEPINE-11-N-ALKYLNORSCOPINE ETHERS HAVING SPASMOLYTIC ACTIVITY

This is a continuation of Ser. No. 471,353, filed Mar. 2, 1983, now abandoned.

The invention herein relates to novel compounds of the formula

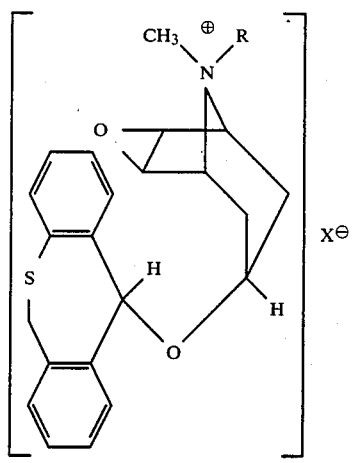

(I)

wherein R represents a linear or branched alkyl having from 1 to 10 carbon atoms and $X^{(-)}$ represents a non-toxic, pharmacologically acceptable anion such as, for example, a halogen or an organic sulfonic acid group. The invention also relates to methods of preparing said compounds, to pharmaceutical compositions containing them as active ingredients, and to methods of using them as spasmolytics or bronchospasmolytics.

The compounds of Formula I may be prepared by reacting compounds of the formula

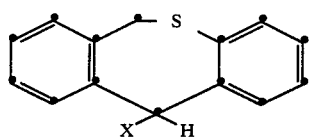

(II)

wherein X represents a group which is easily split off anionically (a so-called "leaving group"), such as a halogen, preferably chlorine or bromine, or a group of an organic sulfonic acid, such as the mesyl or tosyl group, with scopine or N-alkyl-norscopines of the formula

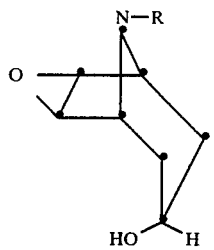

(III)

wherein R is as defined above, to obtain tertiary compounds of the formula

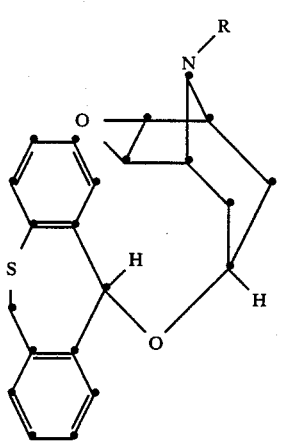

(Ia)

wherein R is as defined above. The compounds of Formula Ia are in turn reacted with conventional quaternization agents of the formula

R—X    (IV)

wherein R and X are as defined above.

The starting compounds of Formula II can be obtained (starting from phthalide) using methods analogous to those described in the literature. Reference may be made to the following publications:

(1) M. Protiva et al., Experientia XVIII (7), 327 (1962);
(2) M. Protiva et al., Collection Czechoslow Chem. Commun. 29, 2176 (1964); and
(3) V. Seidlová et al., Monatshefte der Chemie 96, 653 (1965).

The above-described method of synthesis proceeds, for example, according to the following reaction scheme:

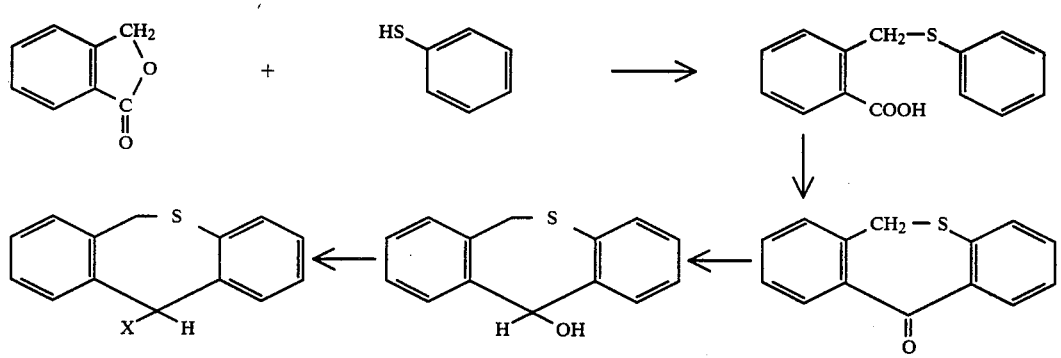

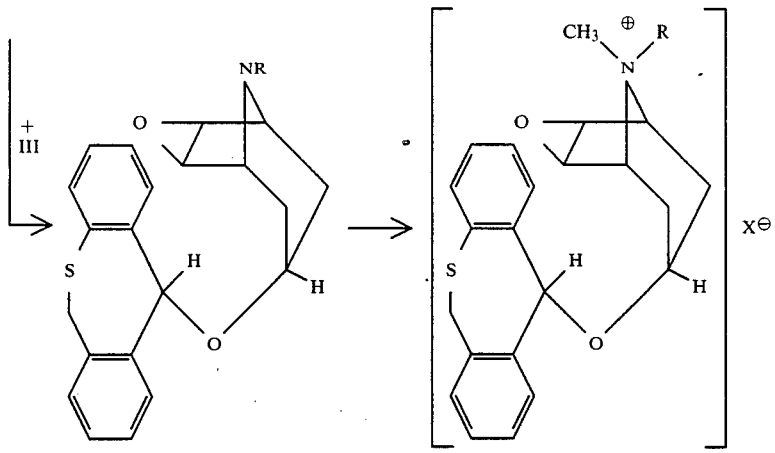

Some of the compounds of Formula III are known from the literature, and some may be obtained by methods which are known per se. The compounds of Formula IV are also known from the literature.

The compounds of Formulas I and Ia have an asymmetric carbon atom in the dibenzothiepine group. Therefore, in the method of synthesis described above, they occur as a racemic mixture of two optically active enantiomers.

When tested on isolated organs and administered in aerosol form to dogs in animal tests, the novel quaternary salts of the invention have been found to have a good anticholinergic activity as well as a good antihistamine activity in a well-balanced ratio which is particularly suitable for use of the substances as bronchospasmolytics. Thus, they are superior to known broncholytics such as the commercially available product ipratropium bromide. Compounds which have proven particularly effective are compounds of Formula I wherein R represents a lower alkyl, such as methyl, ethyl, or isopropyl. The compound 6,11-dihydro-dibenzo-[b,e]-thiepinescopine ether methomethanesulfonate is particularly useful.

The corresponding tertiary intermediate products of Formula Ia also show good activity. However, they tend to be accompanied by side effects such as dryness of the mouth, mydriasis, and the like.

The activity of compounds of the invention was measured by the following methods:

A. SPASOMYLYSIS ON AN ISOLATED ORGAN (Guinea Pig Intestines) IN VITRO

The tests were carried out on the isolated guinea pig rectum using the method described by R. Magnus, Pflü gers Arch. 102, 123 (1904). A section of rectum about 2 cm long taken from a guinea pig which had been killed by a blow on the back of the neck was suspended in an organ bath with Locke-Ringer's solution. The temperature of the organ bath was 35° C. The contractions in the longitudinal muscle caused by a spasmogen (acetylcholine or histamine) were recorded on a kymograph. The spasmolytic agent or control substance (e.g., atropine or diphenhydramine) was added to the organ bath 90 seconds before the spasmogen was administered (preventive method). Both the control substance and the spasmolytic agent to be tested were metered in increasing concentrations so that the activity of the spasmogen was inhibited by from about 10 to 90%.

The tests were carried out using a semi-automatic spasmolysis apparatus (made by Messrs. Bundschuh of Griesheim). Only those preparations for which it was possible to draw up a dosage activity curve both for the control substance and for the spasmolytic substance being tested, on the same section of intestine, were evaluated.

B. BRONCHOSPASMOLYSIS IN DOGS

The purpose of this investigation was to examine the bronchospasmolytic activity in dogs with various forms or administration.

The tests were carried out on male and female beagles weighing from 10 to 14 kg. The anaesthetic used was a mixture of chloralose and urethane (8 gm of chloralose and 40 gm of urethane in 100 ml of distilled water) which was injected in a dosage of 1.5 ml/kg i.v.

Operating procedure

The basic prerequisite for the test arrangement described by H. Knozett and R. Rössler, Arch. exper. Path. und Pharmakol. 195, 71 (1940), is an absolutely leak-tight recording system. First of all, a tracheal tube fitted with an inflatable sleeve was inserted into the test dogs. The blood pressure was measured in the left A. carotis using a Statham transducer. To facilitate intravenous administration, a catheter with a specific capacity was inserted into the right V. femoralis. Before the thorax was opened in the region of the Proc. xiphoideus, the animal was connected to the breathing pump (made by Messrs. Havard, Model 607). The respiratory rate was 16–18/min while the respiratory pressure was 12–16 cm $H_2O$. As in the original method described by Konsett and Rössler, both vagi were severed; bronchospasm was produced by rapid intravenous injection of acetylcholine or histamine at five minute intervals. The blood pressure, bronchospasm, and cardiac rate were recorded on a Grass polygraph.

(a) After intravenous administration

Once constant spasms have been obtained, the test substance or control can be administered intravenously. The substance is always administered one minute before the injection of acetylcholine or histamine. The percentage inhibition of spasms and the duration of effect (half-life), i.e., the time which elapses before the activity of the substance has fallen to half, are evaluated.

(b) After administration of an aqueous aerosol

To enable aerosols to be used in the test arrangement described, a Woulfe flask with a capacity of 5 liters is connected between the respiratory pump and the test animal, as close as possible to the tracheal cannula. This Woulfe flask is provided with three-way taps so that respiration can occur in the following ways:
(i) respiratory pump—first three-way tap—intermediate section—second three-way tap—test animal.
(ii) respiratory pump—first three-way tap—Woulfe flask—second three-way tap—test animal.

The direct route (i) is used for respiration during the test, whereas the route via the flask (ii) is used when the aerosol is being administered.

Preparation and administration of the aerosol

The outlet nozzle of an Inhalette (made by Messrs. Dräger, Lübeck, Model M 12123), is passed through a rubber stopper which fits in the bottom ground glass opening of the Woulfe flask. Then the aqueous solution of the substance to be tested is atomized, and the aerosol is sprayed into the flask. Spraying is effected for 30 seconds with an $O_2$ flow of 15 liters per minute. To prevent atmospheric air from mixing with the aerosol in the flask during administration, the inlet section of the Woulfe flask is connected to a rubber balloon. The air delivered by the respiratory pump inflates the rubber balloon and displaces the aerosol out of the flask so as to deliver it to the test animal. After administration, the three-way taps are turned back so that the respiratory route bypasses the flask. On each administration, five metered doses of aerosol are given 1.5 minutes before the injection of acetylcholine. The percentage inhibition of acetylcholine spasm, the time taken to achieve maximum activity, the half-life, and the effect on the decrease in blood pressure caused by the administration of acetylcholine are evaluated.

Statistical evaluation

A linear quadratic function was assigned to the values using the method of the least squares. The results for the individual batches were tested for significance by variance analysis. The $ED_{50}$ or $EC_{50}$ values were calculated according to Finney with the associated confidence interval (P=0.95).

The compounds of Formula I according to the invention are highly suitable for the treatment of spasms and bronchial spasms due to their pharmacological properties. A quantity of from about 5 to 350 mg (from about 0.07 to 4.67 mg/kg), preferably from about 10 to 300 mg (from about 0.13 to 4.0 mg/kg), of active substance may be suitable as a single dose for oral administration.

Dependent upon the type and body weight of the patient to be treated, on the type and severity of the condition to be treated, on the type of preparation and on the route of administration as well as on the period or interval over which the administration takes place, it may, however, be necessary to deviate from the above dosages. Thus, it may be sufficient in some cases to administer more or less than the above-mentioned amounts of active substance. The optimum dosage and route of administration of the active substances which are necessary in each case can easily be determined by one skilled in the art.

The compounds of the invention can be incorporated, optionally in combination with other active ingredients, in manner known per se, into the usual pharmaceutical preparations such as tablets, coated tablets, capsules, powders, syrups, emulsions, infusions, suppositories, solutions, or suspensions. Such tablets may be produced, for example, by mixing the active substance or substances with known excipients, for example, inert diluents such as calcium carbonate, or magnesium stearate or talc, and/or agents for obtaining delayed release, such as carboxypolymethylene, carboxymethyl cellulose, cellulose acetate phthalate or polyvinyl acetate. Also, the tablets may consist of several layers.

Coated tablets may be produced analogously by coating cores produced in the same way as the tablets with the agents conventionally used for coating tablets, for example, collidone or shellac, gum arabic, talc, titanium dioxide, or sugar. To obtain delayed release or to avoid incompatibilities, the core may also consist of several layers. Similarly, the coating of the tablet may consist of several layers to obtain delayed release, for which the excipients mentioned above with respect to the tablets may be used.

Syrups of the active substances or combinations of active substances according to the invention may additionally contain a sweetener such as saccharin, cyclamate, glycerine, or sugar and a flavor-improving agent such as vanillin or orange extract. They may also contain suspension agents or thickeners such as sodium carboxymethyl cellulose, wetting agents, for example, condensation products of fatty alcohols with ethylene oxide, or preservatives such as 1-hydroxy-benzoates.

Capsules containing one or more active substances or combinations of active substances may be prepared, for example, by mixing the active substances with inert carriers such as lactose or sorbitol and then filling gelatine capsules with the mixture.

Suitable suppositories may be prepared, for example, by the addition of carriers intended for this purpose, such as neutral fats or polyethylene glycol or derivatives thereof.

For treating bronchospasmolytic diseases of the respiratory tract, the active substances are processed in the usual way to make aerosols which are then transferred into spray cans (preferably with a metering device). A therapeutic single dose may be, for example, a quantity of from about 5 to 500 μg, preferably from about 50 to 250 μg, of active substance, corresponding to a content of active substance of from about 0.007 to 1% by weight, based upon the total weight of the aerosol mixture.

As mentioned above, the active substances according to the invention may also be mixed with other active substances. For example, they may be mixed with mucolytics such as bromhexine or cysteine, and may be administered in the form of so-called combined preparations.

The following examples are intended to illustrate the invention and should not be construed as limiting the invention thereto.

EXAMPLES

A. Preparation Examples

Example 1

(a) 6,11-Dihydro-dibenzo-[b,e]-thiepine-11-scopine ether

An amount of 195.5 gm (1.26 mol) of scopine [prepared analogously to and according to G. Werner et al., Tetrahedron Letters 14, 1283 (1967); R. Willstätter et al., Ber. dtsch. chem. Ges. 56, 1079 (1923); J. Meinwald et al., J. Amer. Chem. Soc. 79 665 (1957); and H. L. Schmidt et al., Liebigs Ann. Chem. 688, 228 (1965)] was dissolved in 600 ml of absolute methylene chloride, and at 40° C. a solution of 156.5 gm (0.63 mol) of 11-chloro-6,11-dihydro-dibenzo-[b,e]-thipine (prepared according to the above-mentioned publications of M. Protiva et al. and V. Seidlová et al.) in 200 ml of absolute methylene chloride was added dropwise to the first solution over a period of three hours. After three days at 40° C. the reaction was stopped, and the crystals precipitated (110 gm of scopine hydrochloride) were subjected to suction filtration and then washed with methylene chloride. The combined methylene chloride solutions were extracted first with water then with 600 ml of 1N hydrochloric acid, the methylene chloride phase was washed with water until neutral, and the combined aqueous phases were made alkaline with an aqueous sodium carbonate solution (66 gm of sodium carbonate/200 ml of water) and extracted with methylene chloride. The combined alkaline methylene chloride phases were dried over sodium sulfate, and the methylene chloride was distilled off under reduced pressure.

The distillation residue, 189 gm of white crystals, was recrystallized from acetonitrile (using active charcoal).

Yield: 159.8 gm (69.4% of theory).

White crystals; melting point of 174°-175° C.

The presence of this compound was confirmed by elementary analysis and spectra.

(b) 6,11-Dihydro-dibenzo-[b,e]-thiepine-11-scopine ether methobromide

Two grams (0.0055 mol) of the 6,11-dihydro-dibenzo-[b,e]-thiepine-11-scopine ether obtained in step (a) were reacted with 2.6 gm (0.0275 mol) of methyl bromide at ambient temperature in 35 ml of absolute acetonitrile. After 24 hours the quaternization was stopped. (It has been found that relatively long reaction times and a larger excess of methyl bromide are advantageous when methobromides are prepared on a larger scale.)

The acetonitrile was distilled off, and the residue was taken up in acetonitrile and supersaturated with ether. After this procedure was repeated several times, the solid product was dissolved in water and purified with active charcoal, and the clear solution was then freeze-dried Yield: 1.2 gm (47.4% of theory).

White substance; melting point from 140° C. (with softening).

According to elementary analysis and spectra this compound was present as the monohydrate.

Example 2

6,11-Dihydro-dibenzo-[b,e]-thiepine-11-scopine ether methomethanesulfonate

An amount of 131.3 gm (0.36 mol) of the 6,11-dihydro-dibenzo-[b,e]-thiepine-11-scopine ether prepared according to Example 1(a) was dissolved in 400 ml of absolute methylene chloride, 47.4 gm (0.43 mol) of methyl methanesulfonate were added thereto, and the resulting mixture was reacted at 40° C. under stirring. After six hours a further 19 gm (0.17 mol) of methyl methanesulfonate were added. After a total reaction time of 24 hours, quaternization was stopped. The crystals precipitated were subjected to suction filtration and washed with methylene chloride. The first crude crystals obtained comprised 149.6 gm of white crystals, melting point of 236°-237° C. (decomposition).

A further 8.5 gm (0.08 mol) of methyl methanesulfonate were added to the methylene chloride solution, and the mixture was reacted for a further 24 hours at 40° C. However, total reaction required the addition of a further 8.5 gm (0.08 mol) of methyl methanesulfonate and a reaction time of a further 24 hours. After washing with methylene chloride, second crude crystals were obtained which comprised 18.1 gm of white crystals, melting point of 236°-237° C. (decomposition). The two crude crystal fractions were purified together in methanol using active charcoal, and, after the addition of acetonitrile, the methanolic solution was concentrated under reduced pressure until crystallization occurred.

Yield: 137.7 gm (80.4% of theory).

White crystals; melting point of 236°-237° C. (decomposition).

The presence of this compound was confirmed by elementary analysis and spectra.

EXAMPLE 3

(a)

6,11-Dihydro-dibenzo-[b,e]-thiepine-N-ethylnorscopine ether

The above compound was prepared by a procedure analogous to that of Example 1(a). N-Ethylnorscopine was obtained from the corresponding N-ethylnorscopolamine by a procedure analogous to the procedure given for scopine in Example 1(a).

An amount of 5.5 gm (0.032 mol) of N-ethylnorscopine was dissolved in 50 ml of absolute toluene, and a solution of 4.0 gm (0.016 mol) of 11-chloro-6,11-dihydro-dibenzo-[b,e]-thipine in 30 ml of absolute toluene was added dropwise to the first solution at 80° C. over a period of ten minutes. After six hours at 80° C. the reaction was stopped. The product was worked up as described in Example 1.

Yield: 5.7 gm (93.4% of theory).

White crystals (acetonitrile); melting point of 128°-130° C.

The presence of this compound was confirmed by elementary analysis and spectra.

(b)

6,11-Dihydro-dibenzo-[b,e]-thiepine-11-N-ethylnorscopine ether methobromide

Two grams (0.0053 mol) of the 6,11-dihydro-dibenzo-[b,e]-thiepine-11-N-ethylnorscopine ether prepared in step (a) were reacted with 3.75 gm (0.04 mol) of methyl bromide in 14 ml of aboslute acetonitrile at ambient temperature. After 48 hours quaternization was stopped. The acetonitrile was distilled off, and the residue was taken up in acetontrile and supersaturated with ether. After this procedure was repeated several times, the solid product was dissolved in water and purified with active charcoal, and the clear solution was then freeze-dried.

Yield: 1.5 gm (60.0% of theory).

Solid white substance; melting point from 130° C., with softening.

According to elementary analysis and spectra this compound was present in the form of the hemihydrate.

EXAMPLE 4

6,11-Dihydro-dibenzo-[b,e]-thiepine-11-N-ethylnorscopine ether methomethanesulfonate The above compound was prepared by a procedure analogous to that of Example 2.

EXAMPLE 5

6,11-Dihydro-dibenzo-[b,e]-thiepine-N-n-propylnorscopine ether and the methobromide or methomethanesulfonate The above compounds were prepared by procedures analogous to those of Examples 1 and 2.

EXAMPLE 6

6,11-Dihydro-dibenzo-[b,e]-thiepine-N-isopropylnorscopine ether and the methobromide or methomethanesulfonate The above compounds were prepared by procedures analogous to those of Examples 1 and 2.

B. PHARMACEUTICAL PREPARATIONS

Example 7

Tablets containing 10.0 mg of active substance

Each tablet was compounded from the following ingredients:

| Component | Amount (mg) |
| --- | --- |
| 6,11-dihydro-dibenzo-[b,e]-thiepine-N—ethylnorscopine ether methobromide | 10.0 |
| Lactose | 76.0 |
| Potato starch | 30.0 |
| Gelatine | 3.0 |
| Magnesium stearate | 1.0 |
| TOTAL: | 120.0 |

Method of preparation

The active substance was intensely triturated with ten times the quantity of lactose. This trituration was mixed with the remaining lactose and the potato starch and was granulated with a 10% aqueous solution of gelatine through a 1.5 mm screen. It was then dried at 40° C. The dried granulate was again passed through a 1 mm screen and mixed with the magnesium stearate. Tablets were compressed from the mixture.

Weight of tablet: 120 mg.
Punch: 7 mm, flat, with dividing notch.

Example 8

Coated tablets containing 10.0 mg of active substance

Each tablet core was prepared from the following ingredients:

| Component | Amount (mg) |
| --- | --- |
| 6,11-dihydro-dibenzo-[b,e]-thiepine-11-scopine ether methomethanesulfonate | 10.0 |
| Lactose | 23.0 |
| Corn starch | 14.5 |
| Polyvinylpyrrolidone | 2.0 |
| Magnesium stearate | 0.5 |
| TOTAL: | 50.0 |

Method of preparation

The active substance was intensely triturated with ten times the quantity of lactose. This trituration was mixed with the remaining lactose and the corn starch and was granulated with a 15% aqueous solution of the polyvinylpyrrolidone through a 1 mm screen. The mass, dried at 40° C., was again passed through the screen, mixed with magnesium stearate, and then compressed to form tablet cores.

Weight of core: 50 mg.
Punch: 5 mm, curved.

The tablet cores thus produced were coated in the usual manner with a coating consisting essentially of sugar and talc. The finished coated tablets were polished with beeswax.

Weight of coated tablet: 85 mg.

Example 9

Drops containing 0.125 mg/ml of active substance

One hundred milliliters of drop solution have the following composition:

| Component | Amount |
| --- | --- |
| 6,11-dihydro-dibenzo-[b,e]-thiepine-11-scopine ether methobromide | 0.0125 gm |
| Sodium saccharin | 0.3 gm |
| Sorbic acid | 0.1 gm |
| Ethanol | 30.0 gm |
| Aromatics | 1.0 gm |
| Distilled water q.s. ad | 100.0 ml |

Method of preparation

A solution of the active substance and liquor essence in ethanol was mixed with a solution of the sorbic acid and saccharin in water. The resulting mixture was filtered to remove any suspended particles.

Example 10

Ampules containing 0.5 mg of active substance

Each ampule contained a solution having the following composition:

| Component | Amount |
| --- | --- |
| 6,11-dihydro-dibenzo-[b,e]-thiepine-11-N—ethylnorscopine ether methomethanesulfonate | 0.5 mg |
| Tartaric acid | 150.0 mg |
| Distilled water q.s. ad | 3.0 ml |

Method of preparation

The tartaric acid, polyethylene glycol, and active substance were dissolved successively in the distilled water. The solution was made up to the required volume with distilled water and filtered to sterilize it. The solution was transferred into white 3 ml ampules under a nitrogen atmosphere.

Sterilization: 20 minutes at 120° C.

Example 11

Suppositories containing 0.25 mg of active substance

Each suppository had the following composition:

| Component | Amount (mg) |
| --- | --- |
| 6,11-dihydro-dibenzo-[b,e]-thiepine-N—isopropylnorscopine ether methobromide | 0.25 |
| Lactose | 4.75 |
| Suppository mass (e.g., WITEPSOL ® W 45, available from Chemische Werke Witten GmbH) | 1695.0 |
| TOTAL: | 1700.0 |

Method of preparation

The trituration of the active substance with the lactose was stirred, by means of an immersion homogenizer, into the molten suppository mass, which had been cooled to 40° C. The resulting mixture was cooled to 37° C. and poured into slightly chilled molds.

Weight of suppository: 1.7 gm.

Example 12

Metering aerosol containing active substance

A suitable aerosol mixture would have the following composition:

| Component | Amount (%) |
| --- | --- |
| 6,11-dihydro-dibenzo-[b,e]-thiepine-11-scopine ether methobromide | 0.007-0.7 |
| Surface-active agent such as sorbitane trioleate | 0.5-2.0 |
| Monofluorotrichloromethane and difluorodichloromethane (40:60) q.s. ad | 100 |

Each dose of aerosol spray would contain from about 20 to 150 μg of active substance.

Any one of the other compounds embraced by Formula I, or a combination thereof, may be substituted for the particular active ingredient employed in Examples 7 through 12. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and the various changes and modifications may be made without departing from the spirit of the invention or the scope of the appended claims.

We claim:

1. A compound of the formula

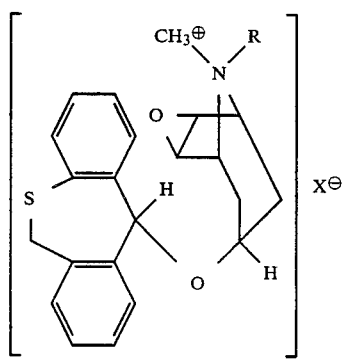

(I)

wherein

R is a linear or branched alkyl having from 1 to 10 carbon atoms and $X^{(-)}$ is a non-toxic, pharmacologically acceptable anion.

2. The compound of claim 1, wherein R is a linear alkyl having from 1 to 3 carbon atoms or a branched alkyl having 3 carbon atoms.

3. The compound of claim 1 which is 6,11-dihydro-dibenzo-[b,e]-thiepine-11-scopine ether methomethanesulfonate.

4. The compound of claim 1 which is 6,11-dihydro-dibenzo-[b,e]-thiepine-11-scopine ether methobromide.

5. The compound of claim 1 which is 6,11-dihydro-dibenzo-[b,e]-thiepine-11-N-ethylnorscopine ether methobromide.

6. The compound of claim 1 which is 6,11-dihydro-dibenzo-[b,e]-thiepine-11-N-ethylnorscopine ether methomethanesulfonate.

7. The compound of claim 1 which is 6,11-dihydro-dibenzo-[b,e]-thiepine-N-n-propylnorscopine ether methobromide.

8. The compound of claim 1 which is 6,11-dihydro-dibenzo-[b,e]-thiepine-N-n-propylnorscopine ether methomethanesulfonate.

9. The compound of claim 1 which is 6,11-dihydro-dibenzo-[b,e]-thiepine-N-isopropylnorscopine ether methobromide.

10. The compound of claim 1 which is 6,11-dihydro-dibenzo-[b,e]-thiepine-N-isopropylnorscopine ether methomethanesulfonate.

11. A compound of the formula

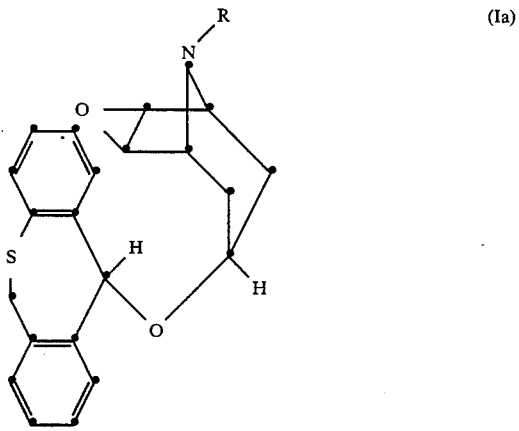

(Ia)

or an acid addition salt thereof with an inorganic or organic acid.

12. A compound of claim 11, wherein the acid addition salt is a non-toxic, pharmacologically acceptable acid addition salt.

13. The compound of claim 11 which is 6,11-dihydro-dibenzo-[b,e]-thiepine-11-scopine ether.

14. The compound of claim 11 which is 6,11-dihydro-dibenzo-[b,e]-thiepine-N-ethylnorscopine ether.

15. The compound of claim 11 which is 6,11-dihydro-dibenzo-[b,e]-thiepine-N-n-propylnorscopine ether.

16. The compound of claim 11 which is 6,11-dihydro-dibenzo-[b,e]-thiepine-N-isopropylnorscopine ether.

17. A pharmaceutical composition for the treatment of spasms or bronchospasms consisting essentially of an effective amount of a compound of claim 1 and conventional galenic excipients and/or pharmaceutical carrier.

18. A method of treating spasms or bronchospasms which comprises administering perorally, parenterally, or rectally to a host in need of such treatment an effective amount of a compound of claim 1.

* * * * *